(12) United States Patent
Van Tasell

(10) Patent No.: US 8,968,209 B2
(45) Date of Patent: Mar. 3, 2015

(54) METHODS AND SYSTEMS FOR HEARING TESTS

(75) Inventor: Dianne J. Van Tasell, Tucson, AZ (US)

(73) Assignee: Unitedheath Group Incorporated, Minnetonka, MN (US)

( * ) Notice: Subject to any disclaimer, the term of this patent is extended or adjusted under 35 U.S.C. 154(b) by 0 days.

(21) Appl. No.: 13/250,781

(22) Filed: Sep. 30, 2011

(65) Prior Publication Data

US 2013/0085411 A1   Apr. 4, 2013

(51) Int. Cl.
*A61B 5/00* (2006.01)
*A61B 5/12* (2006.01)

(52) U.S. Cl.
CPC ........................................ *A61B 5/12* (2013.01)
USPC ......................................................... 600/559

(58) Field of Classification Search
USPC .............. 600/300, 558, 559, 25; 73/584, 585, 73/570; 381/58, 60; 607/1, 55, 56, 57
See application file for complete search history.

(56) References Cited

U.S. PATENT DOCUMENTS

| | | | | |
|---|---|---|---|---|
| 4,038,496 | A  * | 7/1977 | Feezor | 73/585 |
| 4,284,847 | A | 8/1981 | Besserman | 179/1 |
| 6,447,461 | B1 * | 9/2002 | Eldon | 600/559 |
| 6,496,585 | B1 * | 12/2002 | Margolis | 381/60 |
| 6,524,619 | B2 | 2/2003 | Pearson et al. | 424/472 |
| 6,648,820 | B1 * | 11/2003 | Sarel | 600/300 |
| 7,399,282 | B2 | 7/2008 | John et al. | 600/599 |
| 8,031,892 | B2 * | 10/2011 | Andersen et al. | 381/316 |
| 2004/0049125 | A1 | 3/2004 | Nakamur | 600/559 |
| 2005/0018858 | A1 | 1/2005 | John | 381/60 |
| 2007/0003077 | A1 | 1/2007 | Pedersen et al. | 381/106 |
| 2008/0123886 | A1 * | 5/2008 | Andersen et al. | 381/320 |
| 2008/0243211 | A1 | 10/2008 | Cartwright et al. | 607/73 |
| 2009/0154745 | A1 * | 6/2009 | Latzel | 381/314 |
| 2010/0005420 | A1 | 1/2010 | Schneider | 715/833 |
| 2010/0020988 | A1 * | 1/2010 | McLeod | 381/107 |
| 2010/0128911 | A1 * | 5/2010 | Elmedyb et al. | 381/320 |
| 2010/0131032 | A1 * | 5/2010 | Oberhofer et al. | 607/57 |
| 2010/0217149 | A1 | 8/2010 | Harrison et al. | 600/559 |
| 2010/0234757 | A1 * | 9/2010 | Stromsted | 600/559 |
| 2010/0266153 | A1 * | 10/2010 | Gobeli et al. | 381/321 |
| 2011/0009770 | A1 | 1/2011 | Margolis et al. | 600/559 |
| 2011/0029111 | A1 * | 2/2011 | Sabin et al. | 700/94 |
| 2011/0051942 | A1 | 3/2011 | Wilson | 381/60 |

(Continued)

OTHER PUBLICATIONS

Konig et al., article entitled "Course of hearing loss and occurrence of tinnitus," Sep. 7, 2006.*

(Continued)

*Primary Examiner* — Rene Towa
(74) *Attorney, Agent, or Firm* — Norton Rose Fulbright US LLP

(57) ABSTRACT

An apparatus, system, and method for hearing tests are disclosed. In one embodiment, the method determines a set of candidate audiograms for a user. In one embodiment, the method includes estimating the slope of hearing level of a user. The method also includes estimating a pure tone average for the user based on the answers of the user to a questionnaire. The gender of the user is also determined. The gender, estimated slope, estimated pure pone average of the user are used to estimate the most possible audiograms from a set of predetermined candidate audiograms. A hearing aid is programmed based on the estimated audiograms for the user. The programmed hearing aid has several settings, each based on the estimated audiograms, for the user to choose from.

7 Claims, 8 Drawing Sheets

(56) References Cited

U.S. PATENT DOCUMENTS

| | | | |
|---|---|---|---|
| 2011/0075853 A1 | 3/2011 | Anderson | 381/60 |
| 2011/0106508 A1* | 5/2011 | Boretzki | 703/2 |

OTHER PUBLICATIONS

"Check your Hearing," accessed at http://www.rnid.org.uk/how-wehelp/hearing_check/take_online_hearing_check/?at=/hearing-check-home-right-bott-panel/ on Oct. 3, 2011.

"Free Hearing Test," accessed at http://www.freehearingtest.com/test.shtml on Oct. 3, 2011.

"Hearing Frequency Test," accessed at http://www.hearingfrequencytest.com/on Oct. 3, 2011.

"Hearing Test on-line: sensitivity, equal loudness contours and audiometry," accessed at http://www.phys.unsw.edu.au/jw/hearing.html, on Oct. 3, 2011.

"Lloyd's Hearing Aids," accessed at http://lloydhearingaid.com/shopping/audiogram.asp on Oct. 3, 2011.

"Online Hearing Screening" accessed at http://www.phonak.com/com/b2c/en/hearing/recognizing_hearingloss/hearingtest.html, on Oct. 3, 2011.

"Online Hearing Test—Audiology Awareness Campaign," accessed at http://www.audiologyawareness.com/hearingtest.asp on Oct. 3, 2011.

"Online Hearing Test—Hear the World," accessed at http://www.hear-the-world.com/en/recognize-hearing-loss/online-hearing-test.html on Oct. 3, 2011.

"On-Line Hearing Test," accessed at http://www.handtronix.com/webdata/flash/onlinescreener.html on Oct. 3, 2011.

"Online Hearing Test," accessed at http://www.hearing-aid.com/hearing-loss-treatment-considerations/hearing-test on Oct. 3, 2011.

"Online Hearing Test," accessed at http://www.betterhearing.org/hearing_loss/online_hearing_test, accessed on Oct. 3, 2011.

"Siemens hearing test," accessed at http://hearing.siemens.com/en/05-about-hearing/02-understanding-hearing-impairment/01-hearing-loss/01-hearing-test/hearing-test.jsp on Oct. 3, 2011.

"What is your hearing range," accessed at http://www.egopont.com/hearing_tests.php?soundID=1000 on Oct. 3, 2011.

Ciletti and Flamme, "Prevalence of hearing impairment by gender and audiometric configuration: results at the National Health and Nutrition Examination Survey (1999-2004) and the Keokuk County Rural Health Study (1994-1998),"*J. Am. Acad. Audiol.*, 19:672-685, 2008.

Coren and Hakstian, "The development and cross-validation of a self-report inventory to assess pure-tone threshold hearing sensitivity," *Journal of Speech and Hearing Research*, 35:921-928, 1992.

Keidser et al., "The NAL-NL2 prescription procedure," *Audiology 2011*: 1:E24, 2011.

Conlin el al., "Treatment of Sudden Sensorineural Hearing Loss", *Arch. Otolaryngol Head Neck Surg.*, vol. 133, Jun. 2007. Retrieved on Nov. 28, 2012 from http://archotol.jamanetwork.com/article.aspx?articleid=484748.

Kochkin el al., "The validity and Reliability of the BHI Quick Hearing Check: An existing tool that can help guide more consumers to hearing help", hearingreview.com, Nov. 2010. Retrieved on Nov. 28, 2012 from http://www.betterhearing.org/publications/online_hearing/BHI_online_hearing_test_validity.pdf.

International Search Report and Written Opinion issued in PCT Application No. PCT/US2012/057773 on Dec. 11, 2012 (23 pages).

* cited by examiner

METHODS AND SYSTEMS FOR HEARING TESTS

BACKGROUND OF THE INVENTION

1. Field of the Invention

This invention relates to technology applicable to various aspects of audiology including, particularly, that this invention can be used to provide hearing evaluations to clients at various places and to provide hearing aids to clients based on those hearing evaluations.

2. Description of the Related Art

A hearing test provides an evaluation of the sensitivity of a person's sense of hearing. Hearing tests are most often performed by an audiologist using an audiometer. Usually an audiometer may be used to determine a person's hearing sensitivity at different frequencies.

An audiometer hearing test may be administered to a person sitting in a soundproof booth wearing a set of headphones, which is connected to an audiometer. Tones at specific frequencies and set volume levels may be presented to each ear of the user independently. The audiologist or licensed hearing aid specialist may plot the hearing levels of the user, e.g. in decibels, on an audiogram. People having their hearing tested will convey that they have heard the tone by either raising a hand or pressing a button. As the test progresses, the audiologist or hearing aid specialist may plot points on a graph having frequency on the x-axis and hearing level on the y-axis. Hearing level (HL) is referenced to the known average level at which people with normal hearing are able to detect the tones. Once multiple frequencies are tested and plotted, the points may be joined by a line so that one can see at a glance which frequencies are not being heard normally and what degree of hearing loss may be present. Normal hearing at any frequency is typically a hearing level of 15 dB HL or quieter, with worsening hearing as the HL value increases.

After the hearing test, a hearing aid may be prescribed to the user according to the audiogram of the user generated during the hearing test. Hearing aids typically fit in or behind the wearer's ear and may be designed to amplify sound for the wearer.

Some types of hearing tests have been proposed that can be carried out by a user at home. The test may involve Internet connectivity. In traditional home tests, however, devices used for the hearing test, such as a sound card of a computer and headphones, need to be carefully calibrated to ensure that test results are accurate.

SUMMARY OF THE INVENTION

According to different embodiments of this disclosure, hearing tests can be initiated by a user and carried out at various places as the user desires. The user can take hearing tests using a device such as a personal computer or a self-service kiosk. The user can also take a hearing test using portable devices such as but not limited to phones, tablets, gaming devices, music players, portable storage devices such as a USB flash disk (e.g., one connected to a computer), or other platforms. A device may be connected to a hearing test server, e.g. through the Internet, or a standalone device. Moreover, the disclosed embodiments can have a high tolerance to ambient noise.

In one embodiment, a method is presented. The method of this embodiment includes presenting a first stimulus signal at a first frequency and a second stimulus signal at a second frequency to a user where the first frequency and the second frequency are in the human audible frequency range. In other embodiments, additional stimulus signals may be employed, each at a different frequency. The method also includes receiving adjustments to the first stimulus signal and the second stimulus signal to determine a first hearing threshold and a second hearing threshold. A slope of the user's hearing level is calculated based on the difference between the first hearing threshold and the second hearing threshold. The calculated slope is correlated with one or more predetermined candidate audiograms. The predetermined audiograms that do not match the slope within some specified margin of error are eliminated.

In one embodiment, determining a hearing threshold for the user includes determining a first lowest level of a stimulus signal that the user can hear, determining a second lowest level of the stimulus signal that the user can hear, and determining whether the difference between the first lowest level and the second lowest level is within a predetermined range. If the difference is within the predetermined range, the hearing threshold is calculated based on the average of the first lowest level and the second lowest level. If the difference is out of the predetermined range, the procedure is repeated until the difference is within the predetermined range.

In one embodiment, the user is instructed to confirm that he/she can hear the stimulus signal prior to determining the first lowest level of the stimulus signal.

In one embodiment, the slope of a user's hearing level is specified by a range of the slope. Once the slope is calculated, the error in the calculated slope is estimated, and the range of the slope is determined based on the calculated slope and the error in the calculated slope.

In one embodiment, the method also includes calculating a predicted pure tone average for the user based on received questionnaire answers. The questionnaire may be a Better Hearing Institute (BHI) Questionnaire or a Hearing Screening Inventory (HSI) Questionnaire, which are and have been publicly available. In one embodiment, the predicted pure tone average for the user is calculated by solving a regression equation. The predicted pure tone average is correlated with one or more predetermined candidate audiograms for the user, and the uncorrelated candidate audiograms are then eliminated.

In one embodiment, the predicted pure tone average is specified by a range of the predicted pure tone average. Once a predicted pure tone average is calculated for the user, the error in the calculated predicted pure tone average is estimated, and the range for the predicted pure tone average is determined based on the calculated predicted pure tone average and the error in the calculated predicted pure tone average.

In one embodiment, the method further includes determining the gender of the user. The gender of the user is correlated with one or more predetermined candidate audiograms for the user. The candidate audiograms that are not correlated with the gender of the user are eliminated.

In one embodiment, one or more sets of hearing aid parameters are calculated based on each of the one or more correlated candidate audiograms. A hearing aid is programmed for the user by storing one or more sets of hearing aid parameters in the hearing aid. The programmed hearing aid allows the user to choose which set of parameters to use by receiving an input from the user and implementing a selection of a set of hearing aid parameters based on that input.

In one embodiment, a method for hearing test includes determining an audiogram of a user. Determining the audiogram of a user includes providing, to the user, a user interface to adjust a level of a stimulus signal, receiving adjustments to the stimulus signal at a pre-selected frequency, where the frequency is in the human audible frequency range, and determining with a processing device a hearing threshold of the user at the frequency. In one embodiment, the true level of a stimulus signal is randomly associated with a position on a signal level indicator of a user interface.

In one embodiment, a full audiogram of the user is determined, and one or more sets of hearing aid parameters are calculated based on the audiogram.

The term "coupled" is defined as connected, although not necessarily directly, and not necessarily mechanically. The terms "a" and "an" are defined as one or more unless this disclosure explicitly requires otherwise. The term "substantially" and its variations are defined as being largely but not necessarily wholly what is specified as understood by one of ordinary skill in the art, and in one non-limiting embodiment "substantially" refers to ranges within 10%, preferably within 5%, more preferably within 1%, and most preferably within 0.5% of what is specified. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. Furthermore, a device or structure that is configured in a certain way is configured in at least that way, but may also be configured in ways that are not listed.

Other features and associated advantages will become apparent with reference to the following detailed description of specific embodiments in connection with the accompanying drawings.

BRIEF DESCRIPTION OF THE DRAWINGS

The following drawings form part of the present specification and are included to further demonstrate certain aspects of the present invention. The drawings are examples only and are not limiting. The invention may be better understood by reference to one or more of these drawings in combination with the detailed description of specific embodiments presented herein.

DETAILED DESCRIPTION

Various features and advantageous details are explained more fully with reference to the nonlimiting embodiments that are illustrated in the accompanying drawings and detailed in the following description. Descriptions of well known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those having ordinary skill in the art from this disclosure.

In the following description, numerous specific details are provided, such as examples of programming, software modules, user selections, network transactions, database queries, database structures, hardware modules, hardware circuits, hardware chips, etc., to provide a thorough understanding of disclosed embodiments. One of ordinary skill in the art will recognize, however, that embodiments of the invention may be practiced without one or more of the specific details, or with other methods, components, materials, and so forth. In other instances, well-known structures, materials, or operations are not shown or described in detail to avoid obscuring aspects of the invention.

Figure 1:
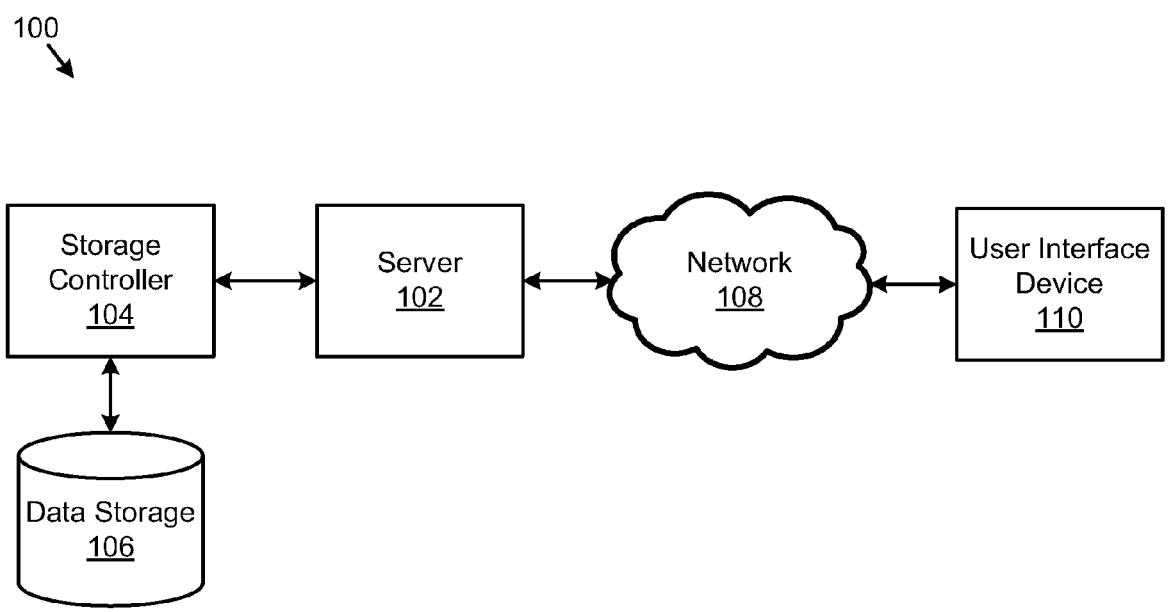
FIG. 1 is a schematic block diagram illustrating one embodiment of a system for hearing tests.

FIG. 1 illustrates one embodiment of a system 100 for hearing tests. The system 100 may include a server 102, a data storage device 104, a network 108, and a user interface device 110. In a further embodiment, the system 100 may include a storage controller 106, or storage server configured to manage data communications between the data storage device 104 and the server 102 or other components in communication with the network 108. In an alternative embodiment, the storage controller 106 may be coupled to network 108. In a general embodiment, the system 100 may instruct a user to input information and receive inputs from the user. The system 100 may also evaluate the input information from the user to determine a hearing condition of the user. The system 100 may output test results to the user. In one embodiment, the system 100 may also program, or assist in programming, a hearing aid for the user based on hearing test results.

The user interface device 110 is referred to broadly and is intended to encompass at least a suitable processor-based device such as a desktop computer, a laptop computer, a Personal Digital Assistant (PDA), a self-service kiosk, a mobile communication device, an organizer device, or the like. In one embodiment, the user interface 110 may be associated with a portable device such as a phone, tablet, gaming device, music player, portable storage device such as a USB flash disk (e.g., one connected to a computer), or other platform. In one embodiment, the user interface 110 may have access to the network 108. In a further embodiment, the user interface device 110 may access the Internet to access a web application or web service hosted by the server 102 and provide a user interface for enabling a user to enter information and receive user input. For example, the user may enter answers to a hearing screening questionnaire. The hearing screening questionnaire may be, or be associated with, questionnaires that have been and are publicly available from various sources such as but not limited to the Better Hearing Institute (BHI) questionnaire or the Hearing Screening Inventory (HSI) questionnaire. The user may also enter his/her gender, age and/or ear disorder information.

The network 108 may facilitate communications of data between the server 102 and the user interface device 110. The network 108 may include any type of communications network including, but not limited to, a direct PC to PC connection, a local area network (LAN), a wide area network (WAN), a modem to modem connection, the Internet, a combination of the above, or any other communications network now known or later developed within the networking arts which permits two or more computers to communicate with another.

In one embodiment, the server 102 is configured to present a stimulus signal to the user and instruct the user to confirm that he/she can hear the signal. The server 102 may also be configured to receive adjustments of the signal from the user and determine the lowest signal level that the user can hear. The server 102 may be also configured to calculate a hearing threshold for the user. A slope of the user's hearing level may be calculated based on the hearing threshold, where the user's hearing level is a graphical plot that specifies the lowest signal level the user can hear at a range of frequencies. In one embodiment, the server 102 may be configured to receive answers of a hearing screening questionnaire from the user. A pure tone average for the user may be calculated based on the user's answers to the questionnaire. In one embodiment the server 102 may also be configured to estimate the user's audiogram from one or more candidate audiograms for the user based on the user input information, slope of hearing level, and/or pure tone average. Additionally, the server may access data stored in the data storage device 104 via a Storage Area Network (SAN) connection, a LAN, a data bus, or the like.

The data storage device 104 may include a hard disk, including hard disks arranged in an Redundant Array of Independent Disks (RAID) array, a tape storage drive comprising a magnetic tape data storage device, an optical storage device, or the like. In one embodiment, the data storage device 104 may store hearing-test-related data, such as a questionnaire, formulae for calculating a user's pure tone average, formulae for estimating a user's audiogram, or the like. The data may be arranged in a database and accessible through Structured Query Language (SQL) queries, or other data base query languages or operations.

In one embodiment, the user interface 110 may be part of a standalone device. In this embodiment, the user interface 110 may work by itself and provide a user interface for enabling a user to enter information and receive user input. In such an embodiment, the user interface device 110 may be configured to carry out the functions of the server 102, storage controller 104, and/or data storage 106. As such, the interface device 110 may not have an Internet connection.

Figure 2:
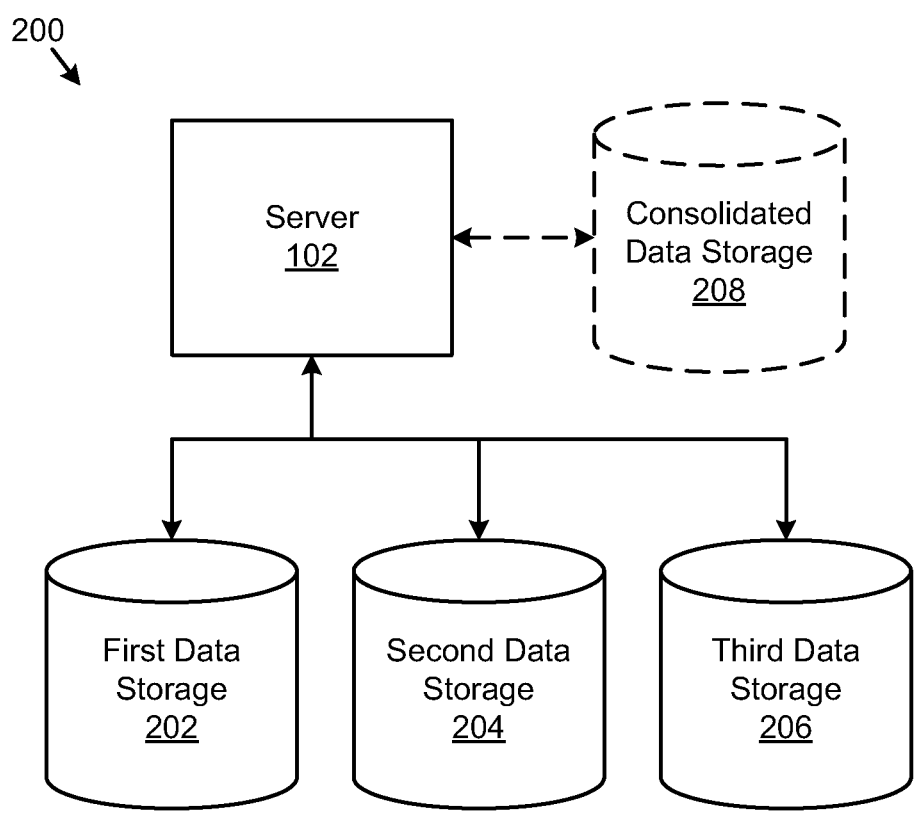
FIG. 2 is a schematic block diagram illustrating one embodiment of a database system for hearing tests.

FIG. 2 illustrates one embodiment of a data management system 200 configured to store and manage data for hearing tests. In one embodiment, the system 200 may include a server 102. The server 102 may be coupled to a data bus 202. In one embodiment, the system 200 may also include a first data storage device 204, a second data storage device 206, and/or a third data storage device 208. In other embodiments, the system 200 may include additional data storage devices (not shown). In such an embodiment, each data storage device 204-208 may host a separate database of answers to a hearing aid screening questionnaire, answers to ear disorder questions, or hearing level information of the user. The storage devices 204-208 may be arranged in a RAID configuration for storing redundant copies of the database or databases through either synchronous or asynchronous redundancy updates.

In various embodiments, the server 102 may communicate with the data storage devices 204-210 over the data bus 202. The data bus 202 may comprise a SAN, a LAN, or the like. The communication infrastructure may include Ethernet, Fibre-Channel Arbitrated Loop (FC-AL), Small Computer System Interface (SCSI), and/or other similar data communication schemes associated with data storage and communication. For example, the server 102 may communicate indirectly with the data storage devices 204-210, the server first communicating with a storage server or storage controller 106.

The server 102 may host a software application configured for hearing tests. The software application may further include modules for interfacing with the data storage devices 204-210, interfacing a network 108, interfacing with a user, and the like. In one embodiment, the server 102 may host an engine, application plug-in, or application programming interface (API). In another embodiment, the server 102 may host a web service or web accessible software application.

Figure 3:
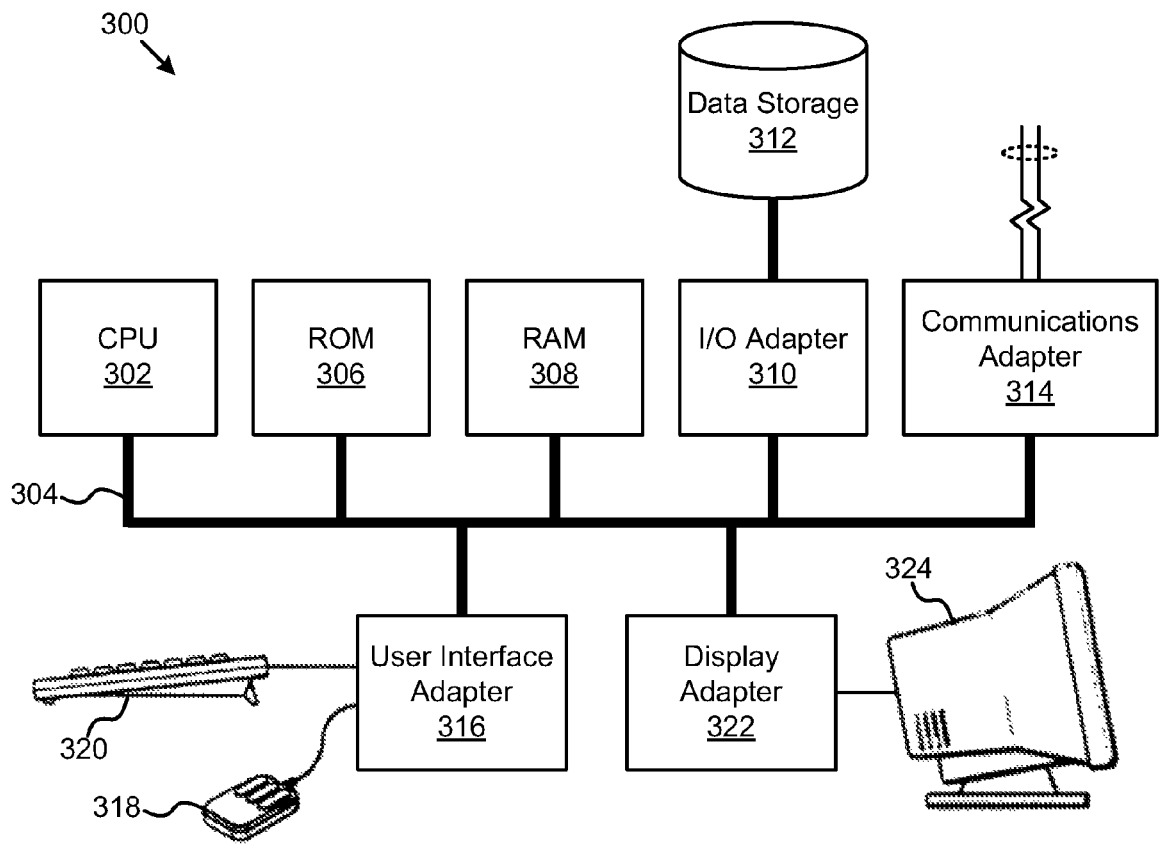
FIG. 3 is a schematic block diagram illustrating one embodiment of a computer system that may be used in accordance with certain embodiments of this disclosure.

FIG. 3 illustrates a system 300 according to certain embodiments of the server 102 and/or the user interface device 110. The central processing unit (CPU) 302 is coupled to the system bus 304. The CPU 302 may be a general purpose CPU or microprocessor. The present embodiments are not restricted by the architecture of the CPU 302, so long as the CPU 302 supports the modules and operations as described herein. The CPU 302 may execute various logical instructions according to disclosed embodiments. For example, the CPU 302 may execute machine-level instructions according to the exemplary operations described below with reference to FIGS. 5-8.

The system 300 also may include Random Access Memory (RAM) 308, which may be SRAM, DRAM, SDRAM, or the like. The system 300 may utilize RAM 308 to store the various data structures used by a software application configured for hearing tests. The system 300 may also include Read Only Memory (ROM) 306 which may be PROM, EPROM, EEPROM, optical storage, or the like. The ROM may store configuration information for booting the system 300. The RAM 308 and the ROM 306 hold user and system 100 data.

The system 300 may include an input/output (I/O) adapter 310, a communications adapter 314, a user interface adapter 316, and a display adapter 322. The I/O adapter 310 and/or user the interface adapter 316 may, in certain embodiments, enable a user to interact with the system 300 in order to input information for hearing tests. In a further embodiment, the display adapter 322 may display a graphical user interface associated with a software or web-based application for hearing tests.

The I/O adapter 310 may connect to one or more storage devices 312, such as one or more of a hard drive, a Compact Disk (CD) drive, a floppy disk drive, a tape drive, to the system 300. In one embodiment, the system 300 may include a communication adapter 314. The communications adapter 314 may be adapted to couple the system 300 to the network 106, which may be one or more of a LAN and/or WAN, and/or the Internet. In an alternative embodiment, the system 300 may be function by itself. The user interface adapter 316 couples user input devices, such as a keyboard 320 and a pointing device 318, to the system 300. The display adapter 322 may be driven by the CPU 302 to control the display on the display device 324.

The present embodiments are not limited to the architecture of system 300. Rather the system 300 is provided as an example of one type of computing device that may be adapted to perform functions of a server 102 and/or the user interface device 110. For example, any suitable processor-based device may be utilized including without limitation, including personal data assistants (PDAs), computer game consoles, and multi-processor servers. In addition, portable devices may take the role of system 300. Moreover, the present embodiments may be implemented on application specific integrated circuits (ASIC) or very large scale integrated (VLSI) circuits. In fact, persons of ordinary skill in the art may utilize any number of suitable structures capable of executing logical operations according to the disclosed embodiments.

Figure 4:
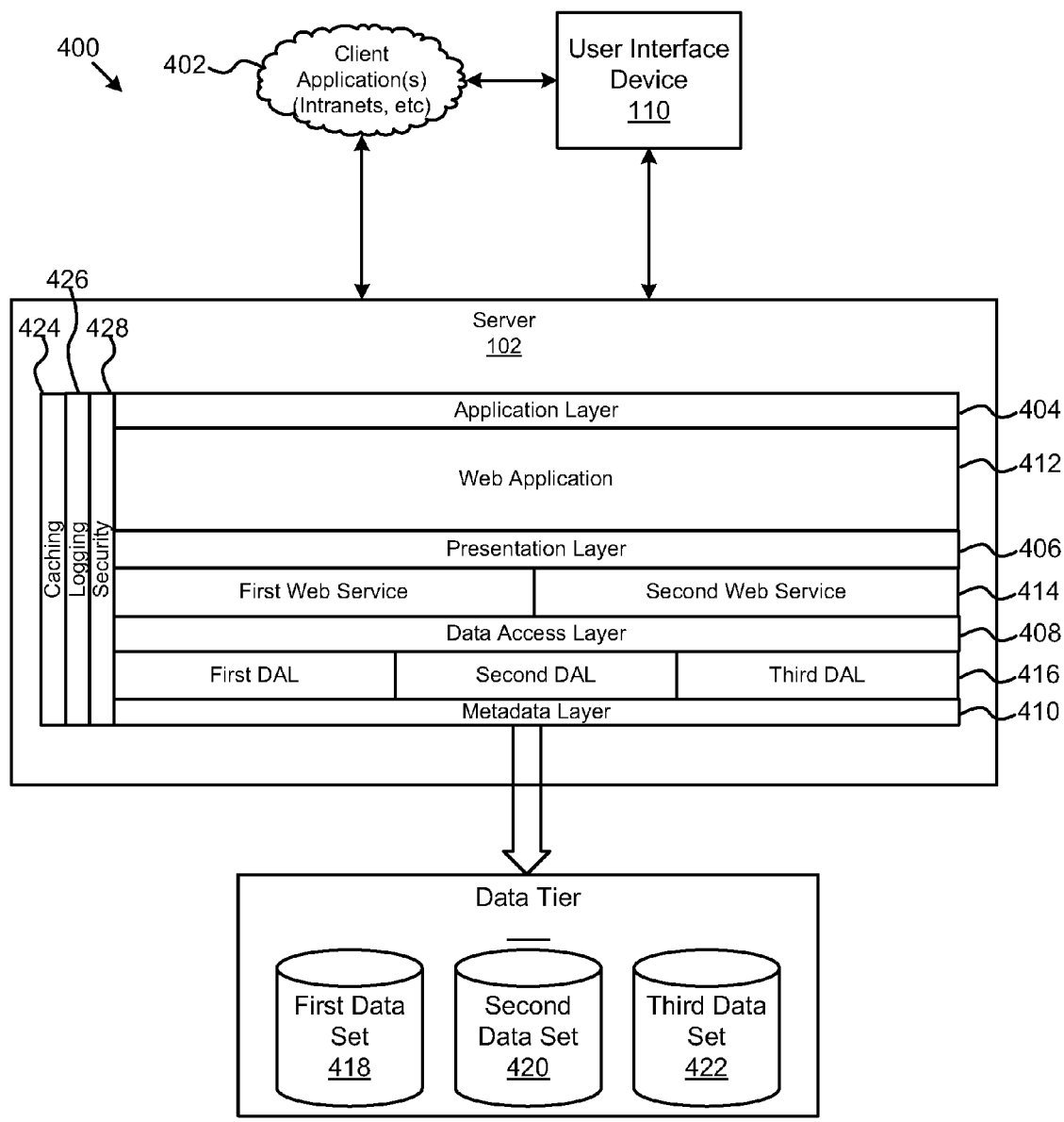
FIG. 4 is a schematic logical diagram illustrating one embodiment of abstraction layers of operation in a system for hearing tests.

FIG. 4 illustrates one embodiment of a network-based system 400 for hearing tests. In one embodiment, the network-based system 400 includes a server 102. Additionally, the network-based system 400 may include a user interface device 110. In still a further embodiment, the network-based system 400 may include one or more network-based client applications 402 configured to be operated over a network 108 including an intranet, the Internet, or the like. In still another embodiment, the network-based system 400 may include one or more data storage devices 104.

The network-based system 400 may include components or devices configured to operate in various network layers. For example, the server 102 may include modules configured to work within an application layer 404, a presentation layer 406, a data access layer 408 and a metadata layer 410. In a further embodiment, the server 102 may access one or more data sets 422-422 that comprise a data layer or data tier. For example, a first data set 422, a second data set 420 and a third data set 422 may comprise a data tier that is stored on one or more data storage devices 204-208.

One or more web applications 412 may operate in the application layer 404. For example, a user may interact with the web application 412 though one or more I/O interfaces 318, 320 configured to interface with the web application 412 through an I/O adapter 310 that operates on the application layer. In one embodiment, a web application 412 may be provided for hearing tests that includes software modules configured to perform steps for hearing tests.

In a further embodiment, the server 102 may include components, devices, hardware modules, or software modules configured to operate in the presentation layer 406 to support one or more web services 414. For example, a web application 412 may access or provide access to a web service 414 to perform one or more web-based functions for web application 412. In one embodiment, web application 412 may operate on a first server 102 and access one or more web services 414 hosted on a second server (not shown) during operation.

For example, a web application 412 may provide the user a way to adjust a stimulus level presented to him/her, or the web application 412 may access a first web service 414 for instructing the user about next steps that he/she should take and a second web service 414 for presenting questionnaires to the user. The web service 414 may receive answers to questions from user or other input information. In response, the web service 414 may output confirmations of data input to the user or instructions to the user for further steps. One of ordinary skill in the art will recognize various web-based architectures employing web service 414 for modular operation of a web application 412.

In one embodiment, a web application 412 or a web service 414 may access one or more of the data sets 418-422 through the data access layer 408. In certain embodiments, the data access layer 408 may be divided into one or more independent data access layers 416 for accessing individual data sets 418-422 in the data tier. These individual data access layers 416 may be referred to as data sockets or adapters. The data access layers 416 may utilize metadata from the metadata layer 410 to provide the web application 412 or the web service 414 with specific access to the data set 412. For example, the data access layer 416 may include operations for performing a query of the data sets 418-422 to retrieve specific information for the web application 412 or the web service 414.

The schematic flow chart diagrams that follow are generally set forth as logical flow chart diagrams. As such, the depicted order and labeled steps are indicative of one embodiment of the present disclosure. Other steps and methods may be employed that are equivalent in function, logic, or effect to one or more steps, or portions thereof, of the illustrated method. Additionally, the format and symbols employed are provided to explain logical steps and should be understood as not limiting the scope of an invention. Although various arrow types and line types may be employed in the flow chart diagrams, they should be understood as not limiting the scope of the corresponding method. Indeed, some arrows or other connectors may be used to indicate only the logical flow of the method. For instance, an arrow may indicate a waiting or monitoring period of unspecified duration between enumerated steps. Additionally, the order in which a particular method occurs may or may not strictly adhere to the order of the corresponding steps shown.

Methods for Providing A Hearing Aid

Figure 5:
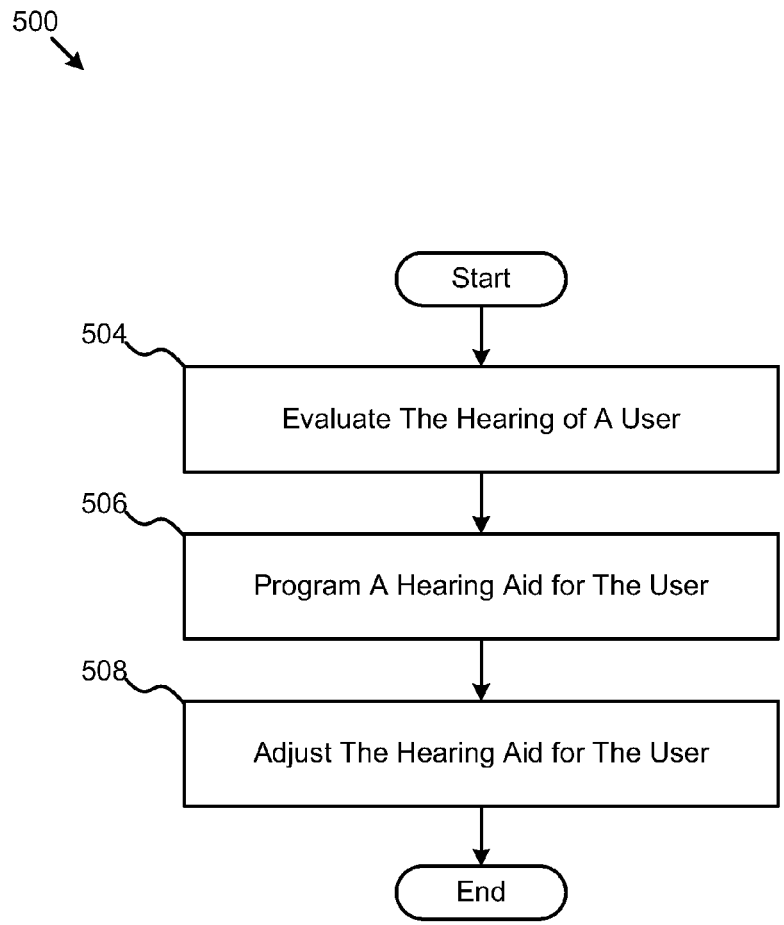
FIG. 5 is a schematic flow chart illustrating one embodiment of a method for providing a hearing aid to a user.

FIG. 5 illustrates one embodiment of a general method 500 for providing a hearing aid to a user. In one embodiment, the method 500 starts with evaluating 504 the hearing of a user. In one embodiment, by evaluating 504 the hearing of the user, one or more audiograms may be estimated for the user. Details about evaluating 504 the hearing of a user are elaborated in FIGS. 6-7. The method 500 may further include programming 506 a hearing aid for the user. In one embodiment, the method 500 may include adjusting 508 the hearing aid after the user has obtained the hearing aid.

In one embodiment, programming 506 a hearing aid for the user may include calculating one or more sets of hearing aid parameters based on estimated audiograms for the user. In one embodiment, hearing aid parameters may be calculated by calling a dynamic link library (DLL) licensed from the National Acoustics Laboratories (NAL-NL2). In one embodiment, programming 506 a hearing aid for the user may further include storing one or more sets of hearing aid parameters to a hearing aid.

In one embodiment, each set of hearing aid parameters may be stored in a memory of the hearing aid. For example, a first set of parameters may be stored in Memory 1 of the hearing aid, a second set of hearing aid parameters may be stored in Memory 2, and a third set of hearing aid parameters may be stored in Memory 3. In such an embodiment, the hearing aid may allow the user to choose which set of parameters he or she prefers (e.g., during usage). These settings may be designed to maximize the chance that the user may use the optimal program and may be designed to offset possible errors in audiogram estimation and estimation of real-ear acoustical characteristics. In one embodiment, the hearing aid parameter fitting for the user may be monaural (Left or Right) or binaural (Left and Right).

In one embodiment, the method 500 may further include adjusting 508 the hearing aid for the user. In one embodiment, the adjustment 508 of the hearing aid for the user may be carried out in a remote-controlled fashion. In such an embodiment, the user may connect to a hearing aid server, e.g. through Internet. The user may be instructed by the server to answer a set of questions about the user's listening experiences with the hearing aid programmed for him/her. Examples of these questions are listed in Table 1. The responses to these questions may indicate if an adjustment to the hearing aid would be beneficial. The nature of the adjustment may also be determined. Based on the answers to the questions, the server may adjust 508 one or more hearing aid parameters stored in the hearing aid over the Internet using dual-tone multi-frequency signaling (DTMF) or other means.

In an alternative embodiment, the adjustment 508 of the hearing aid for the user may be carried out in a standalone fashion. In such an embodiment, a set of questions about the user's listening experiences with the hearing aid, such as those listed in Table 1, may be stored in the hearing aid itself. The user or the hearing aid may initiate a procedure for adjustment. In one embodiment, the hearing aid may be adjusted 508 by the user through buttons or knobs on the hearing aid. In another embodiment, the hearing aid may adjust 508, based the user's answers, one or more sets of hearing aid parameters for the user. This may be done by a program stored in the hearing aid. One of ordinary skill in the art may recognize other alternatives to adjust a hearing aid for a user.

TABLE 1

Common Complaints and Solutions

| Complaint | Most frequently suggested solution |
|---|---|
| Factor 1 | |
| Background noise is too loud. | Decrease low-frequency gain |
| Voices are too loud. | Decrease overall gain |
| My hearing aid is booming. | Decrease low-frequency gain |
| My hearing aid is too loud. | Decrease overall gain |
| Factor 2 | |
| My hearing aid is not loud enough. | Increase overall gain |
| My hearing aid is too soft. | Increase overall gain |
| I can't hear well with my hearing aid. | Increase overall gain |
| My hearing aid is weak. | Increase overall gain |
| Factor 3 | |
| My hearing aid is whistling. | Decrease high-frequency gain |
| My hearing aid sounds tinny. | Decrease high-frequency gain |
| My hearing aid sounds sharp. | Decrease high-frequency gain |
| My hearing aid sounds harsh. | Decrease high-frequency gain |
| Factor 4 | |
| Sounds are painful. | Decrease maximum power output (MPO) |
| Dishes clattering and water running are too loud. | Increase high-frequency compression ratio |
| Loud sounds are too loud. | Decrease MPO |
| Sounds are uncomfortable. | Decrease MPO |
| Factor 5 | |
| My hearing aid is distorted. | Increase MPO |
| Factor 6 | |
| My hearing aid is not clear. | Increase high-frequency gain |
| I can't hear well in noise. | Decrease low-frequency gain |
| My hearing aid makes no difference. | Increase high-frequency gain |
| Factor 7 | |
| My hearing aid is noisy. | Raise low-frequency compression threshold |
| I hear distant sounds better than I hear close sounds. | Raise high-frequency compression threshold |

Hearing Evaluation

Figure 6:
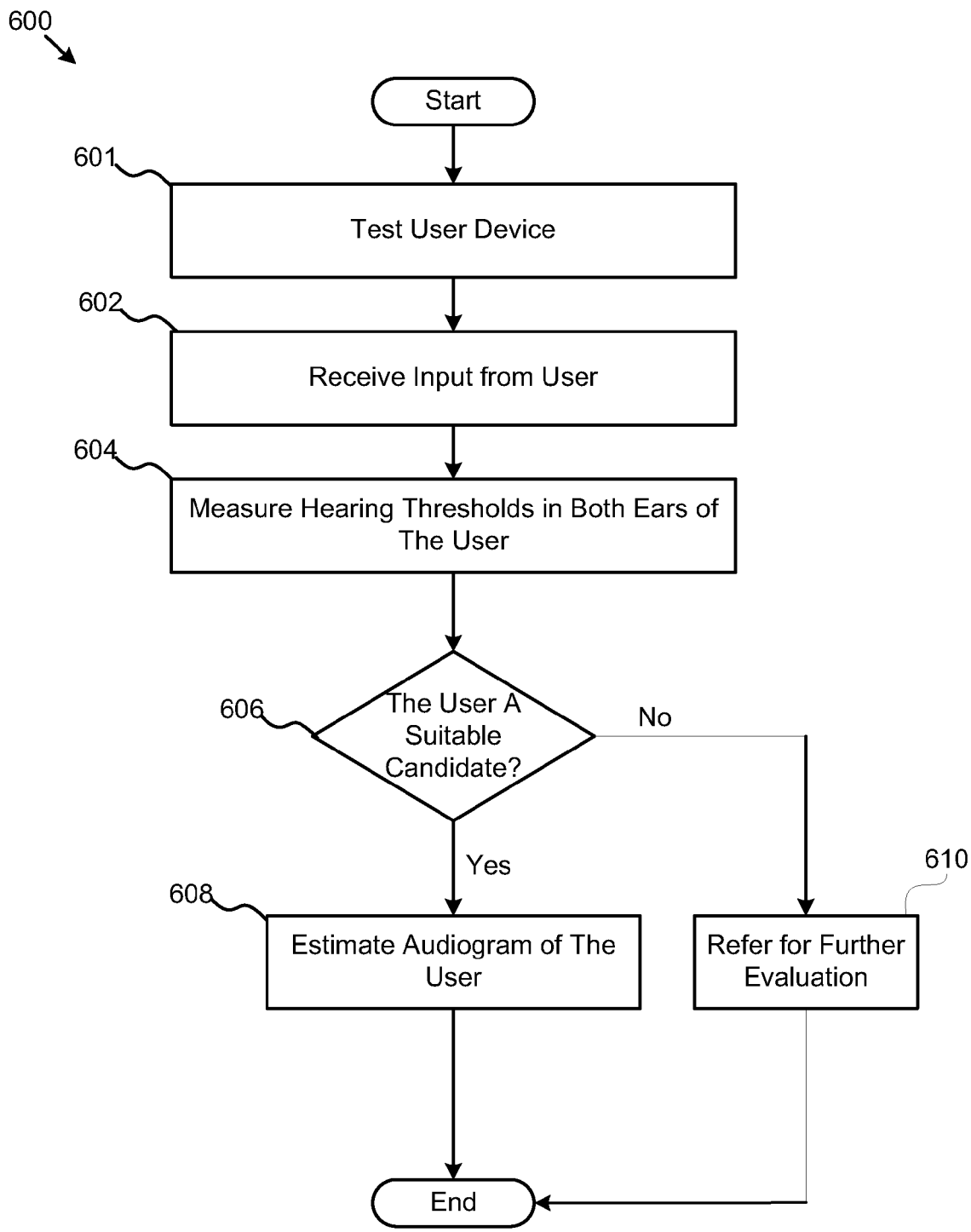
FIG. 6 is a schematic flow chart illustrating one embodiment of a method for evaluating the hearing of a user.

FIG. 6 illustrates one embodiment of a method 600 for evaluating 504 the hearing of a user, as described in FIG. 5. The method 600 may serve as a general method for evaluating 504 the hearing of a user.

In one embodiment, the method 600 may be carried out by a user device. The user device may be phones, tablets, gaming devices, music players, portable storage devices such as a USB flash disk (e.g., one connected to a computer), or other platforms. In one embodiment, the user device may be connected to a hearing evaluation server, e.g. through Internet or the like. In such an embodiment, the server may control the process of hearing evaluation. In an alternative embodiment, the user device may function in a standalone fashion. In such an embodiment, the user device may control the process of hearing evaluation.

In one embodiment, the method 600 for hearing evaluation may be carried out by the user at home or in self-serve kiosks located in a variety of places. In such an embodiment, the method 600 for hearing evaluation may be carried out without the help of an audiologist or physician. This embodiment may be referred as an "In-home Test." Details of this embodiment for method 600 is described in FIG. 7.

In another embodiment, the method 600 for hearing evaluation may be carried out by the user in clinics. In such an embodiment, the method 600 for hearing evaluation may be carried out with the help of an audiologist or physician. This embodiment may be referred as a "Clinical Test." Details of this embodiment for method 600 are described in FIG. 8.

In one embodiment, the method 600 may include testing 601 the user device that is used by the user for hearing evaluation. In one embodiment, testing 601 the user device may include testing a sound card of the user device. Testing 601 the user device may also include testing a set of headphones in use. In one embodiment, testing 601 the user device may include diagnosing acoustical problems in the user device. In a further embodiment, testing 601 the user device may include confirming that a user device is functioning.

In one embodiment, testing 601 user device may include testing the background noise surrounding a user undergoing a hearing evaluation. In one embodiment, the background noise may be measured. If the ambient noise is too high, and the hearing evaluation result may not be reliable, the user may be instructed to terminate the hearing evaluation and/or carry out the hearing evaluation in a less noisy environment.

In one embodiment, the method 600 may be carried out by a portable device kit. The portable device kit may include a USB storage disk, a sound card, a adapter and/or a headphone/ear plug. A program to implement the method 600 may be stored in the USB storage disk. The adapter may be matched to the impedance of the sound card. In one embodiment, the portable device kit may be connected to a user interface such as a personal computer. In one embodiment, the portable device kit may be used for hearing test in a clinic.

In one embodiment, the method may also include receiving 602 input from the user. In one embodiment, the user input may include answers to questions about age, gender, and/or manual dexterity. The gender and/or age of the user may be used for determining the hearing audiogram, and/or calculating hearing aid parameters for the user. The user's answers to manual dexterity questions may be used to determine whether the user is suitable to carry out hearing evaluation and/or obtain a hearing aid by the method 600. Examples of manual dexterity questions are listed in Table 2.

TABLE 2

Manual Dexterity Questions

How much difficulty would you say you have in manipulating buttons on your clothes?

| Never a problem | Sometimes a problem with small buttons | Always difficult |
|---|---|---|

How much difficulty would you say you have in transferring pills from bottles to other containers?

| Never a problem | Sometimes a problem | Always difficult |
|---|---|---|

TABLE 2-continued

Manual Dexterity Questions

How much difficulty do you have putting earrings into a pierced ear?
Never a problem    Sometimes a problem    Always difficult TABLE 2-continued Manual Dexterity Questions How much difficulty do you have placing contact lenses in your eyes?
Never a problem    Sometimes a problem    Always difficult In one embodiment, receiving 602 input from the user may include receiving answers to a set of ear disorder questions. FDA regulations require dispensers to watch for several ear conditions and to refer the client to a physician if any are observed. Examples of ear disorder questions are listed in Table 3. If the client answers positively to any of the ear disorder questions, the method 600 may stop the hearing evaluation. In such a situation, the method 600 may also direct the client to next steps, such as referring 610 the user to an audiologist or physician, etc.

TABLE 3

Ear Disorder Questions

1. Have you experienced any drainage from either of your ears within the last 90 days?
2. Has your hearing changed suddenly during the last 90 days?
3. Does it seem to you that your hearing has gotten a lot worse during the last 90 days?)
4. Have you had any dizzy spells during the last 90 days?
5. Has the hearing in one of your ears gotten noticeably worse in the last 90 days?
6. Do you experience frequent wax build-up in your ears?
7. Do you have any pain or discomfort in your ears?

In one embodiment, receiving 602 input from user may also include receiving user's answers to a questionnaire. In one embodiment, the questionnaire may be one that has been in use for some time and available from a publicly available source. For example, the questionnaire may be a Better Hearing Institute (BHI) questionnaire as shown in Table 4. In an alternative embodiment, the questionnaire may be a Hearing Screening Inventory (HSI) questionnaire as shown in Table 5.

TABLE 4

Hearing Screening Inventory

1. Are you ever bothered by feelings that your hearing is poor?
Never (or almost never)  Seldom  Occasionally  Frequently  Always (or almost always)
2. Is your reading or studying easily interrupted by noises in nearby rooms?
Never (or almost never)  Seldom  Occasionally  Frequently  Always (or almost always)
3. Can you hear the telephone ring when you are in the same room in which it is located?
Never (or almost never)  Seldom  Occasionally  Frequently  Always (or almost always)
4. Can you hear the telephone ring when you are in the room next door?
Never (or almost never)  Seldom  Occasionally  Frequently  Always (or almost always)
5. Do you find it difficult to make out the words in recordings of popular songs?
Never (or almost never)  Seldom  Occasionally  Frequently  Always (or almost always)
6. When several people are talking in a room, do you have difficulty hearing an individual conversation?
Never (or almost never)  Seldom  Occasionally  Frequently  Always (or almost always)
7. Can you hear the water boiling in a pot when you are in the kitchen?
Never (or almost never)  Seldom  Occasionally  Frequently  Always (or almost always)
8. Can you follow the conversation when you are at a large dinner table?
Never (or almost never)  Seldom  Occasionally  Frequently  Always (or almost always)
9. Overall I would judge my hearing in my RIGHT ear to be
Good  Average  Slightly below average  Poor  Very Poor
10. Overall I would judge my hearing in my LEFT ear to be
Good  Average  Slightly below average  Poor  Very Poor
11. Overall I would judge my ability to make out speech or conversations to be
Good  Average  Slightly below average  Poor  Very Poor
12. Overall I would judge my ability to judge the location of things by the sound they are making alone to be
Good  Average  Slightly below average  Poor  Very Poor

TABLE 5

Better Hearing Institute Questionnaire

Strongly disagree ← ... → Strongly agree
0  1  2  3  4

1. I have a problems hearing over the telephone
0    1    2    3    4
2. I have trouble following the conversation when two or more people are talking at the same time
0    1    2    3    4
3. I have trouble understanding things on TV
0    1    2    3    4
4. I have to strain to understand conversations
0    1    2    3    4
5. I have to worry about missing a telephone ring or doorbell
0    1    2    3    4
6. I have trouble hearing conversation in a noisy background such as a crowded room or restaurant
0    1    2    3    4
7. I get confused about where sounds come from
0    1    2    3    4
8. I misunderstand some words in a sentence and need to ask people to repeat themselves
0    1    2    3    4
9. I especially have trouble understanding the speech of women and children
0    1    2    3    4
10. I have trouble understanding the speaker in a large room such as at a meeting or place of worship
0    1    2    3    4
11. Many people I talk to seem to mumble (or don't speak clearly)
0    1    2    3    4
12. People get annoyed because I misunderstand what they say
0    1    2    3    4
13. I misunderstand what others are saying and make inappropriate responses
0    1    2    3    4

TABLE 5-continued

Better Hearing Institute Questionnaire

Strongly disagree ← ... → Strongly agree
0 1 2 3 4

14. I avoid social activities because I cannot hear well and fear
I will reply improperly
0       1       2       3       4
15. Family members and friends have told me they think I may
have a hearing loss
0       1       2       3       4

In one embodiment, the user's answer to each question may be assigned a numerical value (score). In such an embodiment, the score from the questionnaire may be used in at least three ways: (1) combined with other data, the questionnaire may help determine if the user is a suitable candidate for a hearing aid produced by method 600; (2) combined with other data, the questionnaire may help provide initial feedback to the user about the nature of hearing loss if any; (3) the questionnaire may be combined with other data to derive an estimate of the user's audiogram.

In one embodiment, the method 600 may further include verifying 606 whether the user is suitable to proceed with further steps of method 600. If the user is suitable, the method 600 estimates 608 the audiograms of the user. The audiograms of the user may include a left audiogram and a right audiogram, corresponding to the left ear and right ear of the user, respectively. Details about estimating 608 audiograms of the user are described in FIGS. 7-8.

If the user is not suitable, the user may be referred 610 to take further hearing evaluations, such as medical evaluation and/or audiological evaluation with the help of an audiologist or physician.

In one embodiment, possible reasons to conclude that a user is not suitable for method 600 may include:
 a. A suspected medical problem (unless a primary care physician has previously checked the user and concluded that there is no such problem)
 b. Invalid thresholds (for example, if a user could not do a task or if the measured background noise is too high, etc.)
 c. Asymmetrical hearing loss (for example, if a user is too difficult to fit or if a user may require undue custom modifications. These may be an indicator of a medical problem that needs immediate attention.)
 d. Hearing loss outside of a fitting range of hearing aids.

In one embodiment, the method 600 may further include estimating 608 one or more audiograms of the user. In one embodiment, hearing thresholds may be measured 604 at only two frequencies in the human audible frequency range. In such an embodiment, a slope of the hearing level may be calculated. The slope information may be combined with other data, such as gender and estimated pure tone average of the user, to provide estimates 608 of the user's audiogram. Details of this embodiment are described in FIG. 7. In other embodiments, hearing thresholds may be measured at more than two frequencies in the human audible frequency range. For example, three, four, five, six, seven, eight, nine, ten, etc. frequencies may be used, all in accordance with steps disclosed herein and illustrated, for example, in FIG. 7.

In other embodiments, hearing thresholds may be measured 604 for a range of frequencies in the human audible frequency range. In such an embodiment, a full audiogram of the user may be estimated 608. Details of this embodiment are described in FIG. 8.

Figure 7:
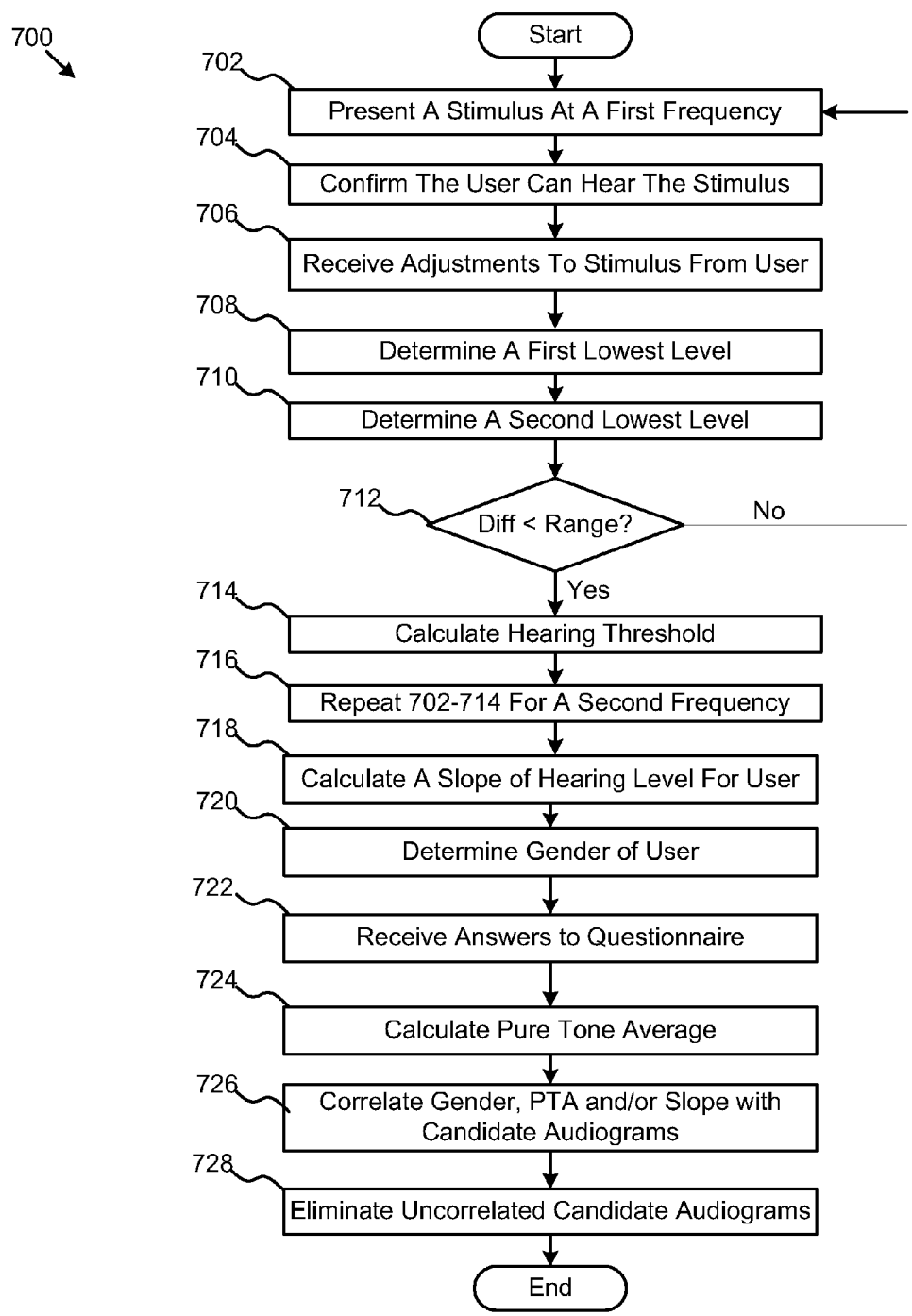
FIG. 7 is a schematic flow chart illustrating one embodiment of a method for evaluating the hearing of a user.

FIG. 7 illustrates one embodiment of a method 700 for estimating 608 audiograms of a user. As described in FIG. 6, this embodiment may be referred as the "In-home Test". In one embodiment, the method 700 may include presenting 702 a stimulus signal at a first frequency to a user. The first frequency may be in the human audible frequency range. In one embodiment, the first frequency may be at 2 kHz or 4 kHz. The first stimulus signal may be at a high level, e.g. 30 dB, so that the user can clearly hear the stimulus. In one embodiment, the method 700 may also include confirming 704 that the user can clearly hear the stimulus signal.

In one embodiment, a user interface may be provided to the user. The user interface may include mechanisms, e.g. a slider, a wheel, or a window, for the user to adjust the level of a stimulus signal. For example, the user may turn up or turn down the level of a stimulus signal by moving a button on a slider. In one embodiment, the user interface may also allow the user to receive instructions and respond to instructions. For example, instructions such as "turn up the stimulus level until you can hear the signal" may be presented to the user through the user interface. Questions may also be presented to the user through the user interface, and the user may also be allowed to enter information through the user interface.

In one embodiment, the method 700 may include receiving 706 adjustments to the stimulus signal from the user. For example, the user may be instructed to adjust (turn down) the signal level until he/she cannot hear the signal. The user may also be instructed to adjust (turn up) the signal level until he/she can just hear the signal. In one embodiment, the true signal level may be randomly associated with a position on the signal level indicator of the user interface. In this way, the user may be prevented from associating the level of the stimulus signal with a specific position on the signal indicator.

In one embodiment, the method 700 may include determining 708 a first lowest level of the stimulus signal that the user can hear. In such an embodiment, the user may be instructed to turn down the stimulus after he/she confirms that he can clearly hear the stimulus. The stimulus may be then turned down by 10 dB. Afterwards, the user may be instructed to turn up the stimulus until he/she can hear the stimulus signal again. The method 700 may determine 708 this stimulus level as the first lowest level.

In one embodiment, the method 700 may include determining 710 a second lowest level of the stimulus signal that the user can hear. In one embodiment, the second lowest level can be determined 710 in a similar way that the first lowest level is determined.

In one embodiment, the method 700 may further include determining 712 whether the difference between the first lowest level and the second lowest level is within a predetermined range. For example, the predetermined range may be 5 dB. Other predetermined ranges may be different values; for example, 1, 2, 3, 4, 6, 7, 8 dB etc. may be used. If the difference is within the predetermined range, a first hearing threshold for the user may be calculated 714 as the average between the first lowest level and the second lowest level. If the difference between the first and second lowest level is out of the predetermined range, steps 702-712 may be repeated until the difference is within the range. In one embodiment, the procedure for measuring the user's hearing threshold may be carried out for both ears of the user.

By verifying whether the difference between the first lowest level and the second lowest level is within a predetermined range, the accuracy of the measured hearing threshold may be improved.

In another embodiment, steps 702-712 may be repeated for a plurality of times to generate a plurality of lowest levels that the user can hear. In this embodiment, a plurality of lowest levels can be used in a similar fashion as the case with two lowest levels to improve the accuracy of the measured hearing threshold for the user. One of ordinary skill in the art may recognize other methods to improve the accuracy of the measured hearing threshold for a user.

In one embodiment, the steps 702-714 for calculating a hearing threshold may be referred as Method of Adjustment. In an alternative embodiment, a hearing threshold may be calculated by a Hughson-Westlake procedure (Carhart & Jerger, 1952).

In one embodiment, the steps 702-714 may be repeated 716 for at least a second stimulus at a second frequency to calculate a second hearing thresholds for the user. The second frequency may be in the human audible frequency range. In one embodiment, the second frequency may be at 2 kHz or 4 kHz. In one embodiment, therefore, a first frequency is 2 kHz while the second frequency is 4 kHz. A slope of the user's hearing level may be calculated 718 based on the first and second hearing thresholds of the user. In one embodiment, the slope may be calculated 718 as the difference between the second and first hearing thresholds, e.g. the hearing threshold at 4 kHz minus the hearing threshold at 2 kHz.

In another embodiment, stimulus signals at more than two frequencies may be used to measure multiple hearing thresholds for the user, where the frequencies are in the human audible frequency range. In such an embodiment, two or more of the measured hearing thresholds may be used to calculate the slope of the user's hearing level. For example, one pair of the measured hearing thresholds may be selected to calculate the slope. Alternatively, several pairs of the measured hearing thresholds may be selected to calculate several slopes and the slopes may be averaged to generate a final slope. One of ordinary skill in the art may recognize other alternatives to use the multiple measured thresholds to calculate a slope of hearing level for a user.

In one embodiment, a person's audiogram may be characterized by a plurality of modal audiograms (candidate audiograms). Prior research by others has shown that the audiograms of men and women can be characterized with only a small number of modal audiograms, e.g. 11 modal audiograms for men and 6 modal audiograms for women (Ciletti & Flamme, 2008). In such an embodiment, the calculated slope may be correlated 726 with one or more candidate audiograms. For example, the candidate audiograms whose slopes match the calculated slope are correlated with the calculated slope. The candidate audiograms that are not correlated with the calculated slope may be then eliminated 728.

In common practices of hearing evaluation, a full audiogram is usually measured for a user. In this case, the user devices used for the hearing test, such as the sound card and the headphone, need to be carefully calibrated to guarantee that the test results are accurate. In contrast, the slope of the user's hearing level may be used in method 700, where the slope is calculated based on the difference between at least a first hearing threshold at a first frequency and a second hearing threshold at a second frequency.

In a further embodiment, an error in the calculated slope may be estimated. For example, the error in the calculated slope may be estimated based on the errors in the headphone or sound card the user is using, or the ambient noise present at the hearing test. For example, the slope error can be estimated by computing the standard error of slope measured in a laboratory on an acoustic mannequin for 7 brands of earphones, 3 instances each, right/left, removed and replaced twice. In such an embodiment, a range of the slope may be determined, e.g. based on the calculated slope and the estimated error in the calculated slope.

In one embodiment, the range of the slope may be determined as the calculated slope +/−estimated error in the slope. For example, if the calculated slope is 19, and the estimated error in the slope is 7, then the range of the slope is from 12 to 26. In one embodiment, the true slope of the user's hearing level may be assumed to lie in the range of the slope with equal probability, i.e. uniformly distributed. In such an embodiment, the range of the slope may be correlated with one or more candidate audiograms. For example, the candidate audiograms whose slopes match the range of slope are correlated. The candidate audiograms that are not correlated may be then eliminated 728.

In one embodiment, the method 700 may further include determining 720 the gender of the users. The gender of the user may be correlated 728 with one or more candidate audiograms. For example, if the gender is male, then candidate audiograms for males are then correlated. The candidate audiograms that are not correlated may be eliminated 728.

In one embodiment, the method 700 may further include receiving 722 answers to a questionnaire from a user. In one embodiment, the questionnaire may be a BHI questionnaire. In an alternative embodiment, the questionnaire may be a HSI questionnaire. Other questionnaires or similar methods of obtaining input may be used as well. The answer to each question of the questionnaire may be assigned a value, i.e. a numerical number. A regression model may be applied to model the relationship between the user's answers to the questionnaire and the user's pure tone average (i.e. average hearing loss). In one embodiment, the regression model may be a linear regression model. With a regression model, a regression equation may be solved to calculate 724 a pure tone average of the user.

In one embodiment, the calculated pure tone average may be correlated 726 with one or more candidate audiograms. For example, the candidate audiograms whose average pure tones match the calculated pure tone average are correlated. The candidate audiograms that are not correlated with the calculated pure tone average may be then eliminated 728.

In a further embodiment, an estimation error for the regression equation may be calculated. For example, the fully measured audiograms of a large number of people and their responses to a questionnaire can be used to calculate a model for the relationship between actual audiograms and responses to the questionnaire. With the known model, the root mean square error or standard error of the linear regression may be calculated. In one embodiment, data from a cohort of about 200 hearing impaired people may be used to ensure a regression equation is correct.

In one embodiment, a range of pure tone averages may be determined based on the calculated pure tone average and estimated error in pure tone average. For example, if the error in the calculated pure tone average is estimated to be 12 dB, the range of the pure tone average may be determined as the calculated pure tone average +/−12 dB. The actual pure tone average may be assumed to lie in the range with equal probability, i.e. uniformly distributed. In such an embodiment, the range of the pure tone average may be correlated with one or more candidate audiograms. For example, the candidate audiograms whose pure tone averages match the range of pure tone average are correlated. The candidate audiograms that are not correlated may be then eliminated 728.

In one embodiment, only the candidate audiograms that are correlated to the gender, calculated slope, and calculated pure tone average may be considered. In one embodiment, if there are more than three candidate audiograms correlated to the gender, calculated slope, and calculated pure tone average, further steps may be taken to further eliminate one or more candidate audiograms. In one embodiment, further eliminations may be based on prescribed NAL gain from National Acoustic Laboratories.

Figure 8:
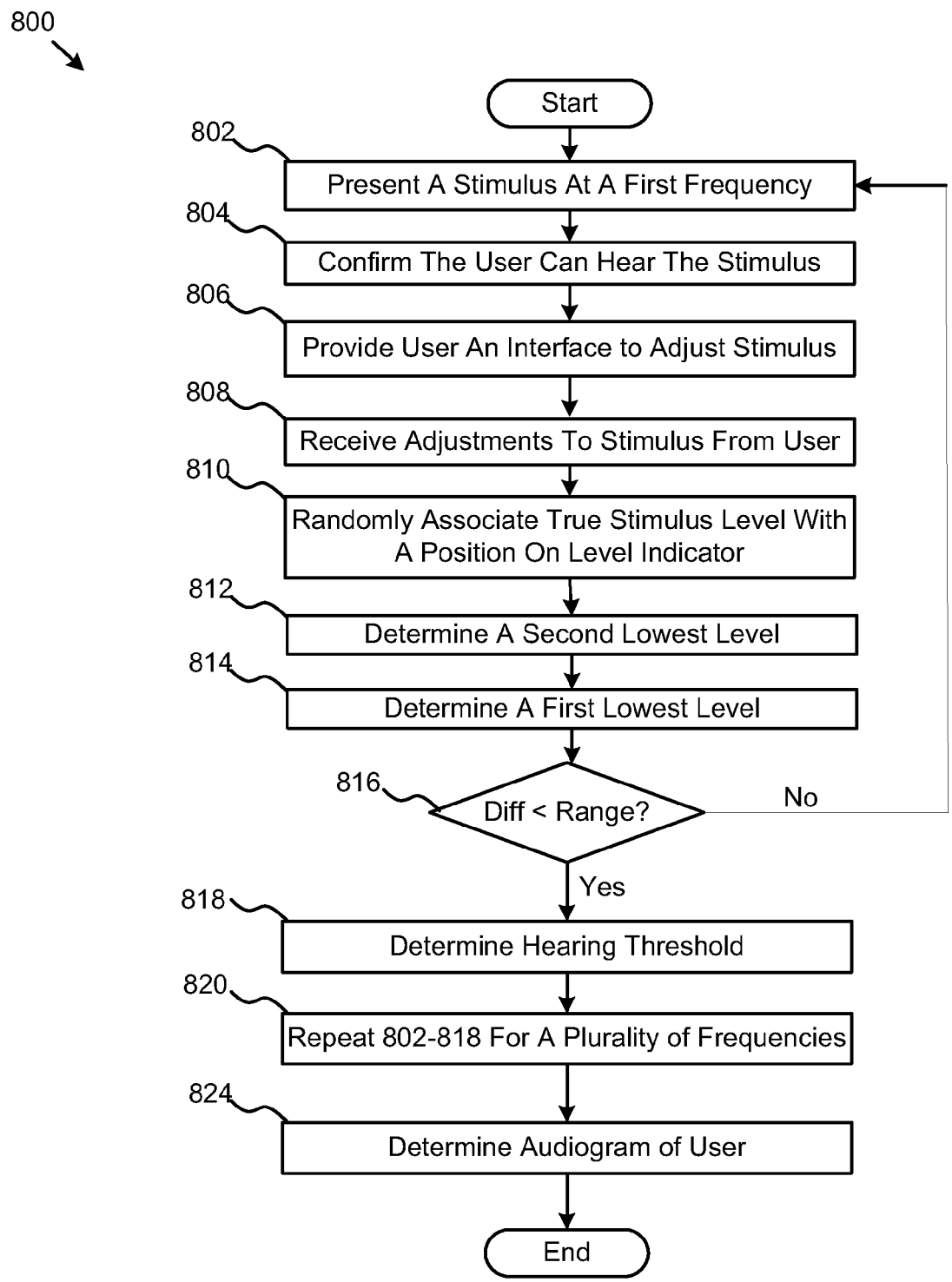
FIG. 8 is a schematic flow chart illustrating one embodiment of a method for evaluating the hearing of a user.

FIG. 8 illustrates another embodiment of a method for estimating 608 audiograms of a user. As described in FIG. 6, this embodiment may be referred as a "Clinical Test." The Clinical Test may be used, for example, when a billing under CPT Code 92552 is required. In one embodiment, the method 800 includes determining a threshold for the user at a frequency. The frequency may be in the human audible frequency range. In one embodiment, determining a threshold for the user may include steps 802-818, as shown in FIG. 8. In one embodiment, the steps 802-818 for determining a threshold for the user may be carried out in a similar fashion as in step 702-714 of FIG. 7.

In one embodiment, steps 802-818 may be repeated 820 at a plurality of frequencies in the human audible frequency range, with the hearing threshold determined for the user at those frequencies. Afterwards, a full or partial audiogram of the user may be determined 824 based on the hearing thresholds.

EXAMPLE

Candidate audiograms are selected from the cluster audiograms for symmetrical losses for men and women reported in Ciletti & Flamme (2008). The candidate audiograms for males and females are modeled by the hearing levels at frequencies 500 Hz, 1 kHz, 2 kHz, 3 kHz, 4 kHz, and 6 kHz. Candidate audiograms for males and females are shown in Table 6 and Table 7 respectively.

TABLE 6

Modal Audiograms for Male

| Male | 500 | 1000 | 2000 | 3000 | 4000 | 6000 |
|---|---|---|---|---|---|---|
| A11− | 2 | −1 | −1 | −1 | 0 | 4 |
| A11 | 7 | 4 | 4 | 4 | 6 | 11 |
| A11+ | 12 | 9 | 9 | 9 | 12 | 18 |
| A19− | 4 | 3 | 3 | 5 | 8 | 12 |
| A19 | 10 | 8 | 8 | 10 | 14 | 19 |
| A19+ | 16 | 13 | 13 | 15 | 20 | 26 |
| A33− | 4 | 4 | 5 | 14 | 25 | 20 |
| A33 | 9 | 8 | 11 | 22 | 33 | 28 |
| A33+ | 14 | 12 | 17 | 30 | 41 | 36 |
| A47− | 5 | 5 | 9 | 33 | 39 | 29 |
| A47 | 12 | 13 | 20 | 42 | 47 | 39 |
| A47+ | 19 | 21 | 31 | 51 | 55 | 49 |
| A59− | 6 | 6 | 7 | 16 | 29 | 43 |
| A59 | 13 | 13 | 15 | 24 | 38 | 53 |
| A59+ | 20 | 20 | 23 | 32 | 47 | 63 |
| B26− | 13 | 13 | 14 | 14 | 17 | 18 |
| B26 | 20 | 20 | 22 | 22 | 24 | 26 |

TABLE 6-continued

Modal Audiograms for Male

| Male | 500 | 1000 | 2000 | 3000 | 4000 | 6000 |
|---|---|---|---|---|---|---|
| B26+ | 27 | 27 | 30 | 30 | 31 | 34 |
| B74− | 10 | 12 | 35 | 56 | 60 | 66 |
| B74 | 17 | 20 | 45 | 63 | 68 | 74 |
| B74+ | 24 | 28 | 55 | 70 | 76 | 82 |
| B82− | 9 | 9 | 12 | 34 | 57 | 70 |
| B82 | 17 | 16 | 21 | 48 | 68 | 80 |
| B82+ | 25 | 23 | 30 | 62 | 79 | 90 |
| B91− | 12 | 19 | 47 | 67 | 76 | 83 |
| B91 | 21 | 29 | 58 | 76 | 85 | 91 |
| B91+ | 30 | 39 | 69 | 85 | 94 | 99 |
| C55− | 22 | 30 | 33 | 39 | 42 | 45 |
| C55 | 35 | 41 | 46 | 49 | 52 | 55 |
| C55+ | 48 | 52 | 59 | 59 | 62 | 65 |
| D78− | 25 | 37 | 49 | 58 | 62 | 69 |
| D78 | 39 | 48 | 59 | 65 | 69 | 77 |
| D78+ | 53 | 59 | 69 | 72 | 76 | 85 |
| E109− | 37 | 49 | 72 | 83 | 90 | 96 |
| E109 | 55 | 64 | 81 | 95 | 100 | 107 |
| E109+ | 73 | 79 | 90 | 107 | 110 | 118 |

TABLE 7

Modal Audiograms for Female

| Female | 500 | 1000 | 2000 | 3000 | 4000 | 6000 |
|---|---|---|---|---|---|---|
| A11− | 2 | −1 | 0 | −2 | −1 | 4 |
| A11 | 7 | 4 | 5 | 3 | 5 | 11 |
| A11+ | 12 | 9 | 10 | 8 | 11 | 18 |
| A22− | 6 | 4 | 4 | 5 | 7 | 15 |
| A22 | 12 | 9 | 9 | 10 | 13 | 22 |
| A22+ | 18 | 14 | 14 | 15 | 19 | 29 |
| A48− | 7 | 5 | 7 | 10 | 15 | 29 |
| A48 | 14 | 11 | 14 | 18 | 24 | 39 |
| A48+ | 21 | 17 | 21 | 26 | 33 | 49 |
| B29− | 13 | 12 | 14 | 15 | 16 | 21 |
| B29 | 22 | 20 | 22 | 22 | 25 | 29 |
| B29+ | 31 | 28 | 30 | 29 | 34 | 37 |
| B66− | 14 | 15 | 21 | 29 | 36 | 49 |
| B66 | 24 | 25 | 31 | 39 | 46 | 60 |
| B66+ | 34 | 35 | 41 | 49 | 56 | 71 |
| D84− | 33 | 40 | 48 | 52 | 56 | 68 |
| D84 | 50 | 55 | 61 | 63 | 69 | 82 |
| D84+ | 67 | 70 | 74 | 74 | 82 | 96 |

A lookup table may be generated to obtain the estimated audiograms for a user. Example cells from a lookup table are depicted in Table 8. In some embodiments, a different lookup table may be generated for male users and female users. The slope average (reflected in the first column) is the measured slope average across ears. Table entries were generated as follows: Each of the cluster audiograms was characterized by a four-frequency pure tone average (reflected in the first row) with average thresholds at 500 Hz, 1000 Hz, 2000 Hz, and 4000 Hz. The slope of hearing level is calculated as the hearing threshold at 4 kHz minus the hearing threshold at 2 kHz.

TABLE 8

Lookup Table for Male to Obtain Estimated Audiograms

| Male | 11 | 12 | 13 | 14 | 15 | 16 |
|---|---|---|---|---|---|---|
| 16 | A33, A59, A47 | A33, A59, A47 | A33, A59, A47 | A33, A59, A47 | A33, A59, A47 | A33, A59, A47 |
| 17 | A33, A59, A47 | A33, A59, A47 | A33, A59, A47 | A33, A59, A47 | A33, A59, A47 | A33, A59, A47 |
| 18 | A33, A59, A47 | A33, A59, A47 | A33, A59, A47 | A33, A59, A47 | A33, A59, A47 | A33, A59, A47 |
| 19 | A33, A59, A47 | A33, A59, A47 | A33, A59, A47 | A33, A59, A47 | A33, A59, A47 | A33, A59, A47 |
| 20 | A33, A59, A47 | A33, A59, A47 | A33, A59, A47 | A33, A59, A47 | A33, A59, A47 | A33, A59, A47 |
| 21 | A33, A59, A47 | A33, A59, A47 | A33, A59, A47 | A33, A59, A47 | A33, A59, A47 | A33, A59, A47 |

TABLE 8-continued

Lookup Table for Male to Obtain Estimated Audiograms

| Male | 11 | 12 | 13 | 14 | 15 | 16 |
|---|---|---|---|---|---|---|
| 22 | A33, A59, A47 | A33, A59, A47 | A33, A59, A47 | A33, A59, A47 | A33, A59, A47 | A33, A59, A47 |
| 23 | A33, A59, A47 | A33, A59, A47 | A33, A59, A47 | A33, A59, A47 | A33, A59, A47 | A33, A59, A47 |
| 24 | A33, A59, A47 | A33, A59, A47 | A33, A59, A47 | A33, A59, A47 | A33, A59, A47 | A33, A59, A47 |
| 25 | A33, A59, A47 | A33, A59, A47 | A33, A59, A47 | A33, A59, A47 | A33, A59, A47 | A33, A59, A47 |
| 26 | A33, A59, A47 | A33, A59, A47 | A33, A59, A47 | A33, A59, A47 | A33, A59, A47 | A33, A59, A47 |
| 27 | A33, A59, A47 | A33, A59, A47 | A33, A59, A47 | A33, A59, A47 | A33, A59, A47 | A33, A59, A47 |
| 28 | A33, A59, A47 | A33, A59, A47 | A33, A59, A47 | A33, A59, A47 | A33, A59, A47 | A33, A59, A47 |
| 29 | A33, A59, A47 | A33, A59, A47 | A33, A59, A47 | A33, A59, A47 | A33, A59, A47 | A33, A59, A47 |

Regression equation predicting four-frequency pure tone average from the HSI score (Coren & Hakstain, 1992) was derived using questionnaire and audiogram data from 50 subjects at University of Minnesota, where the regression equation was derived to be $$\text{Predicted pure tone average} = (1.23 * (\text{HSI score})) - 15.4$$

Standard error (SE) of prediction measured to be 9.65 dB, so expected error set at +1.2 (SE), which corresponds to roughly an 80% point on normal distribution.

Error for slope was estimated by computing standard deviation (SD) of the slope measured in a laboratory on an acoustic mannequin for 7 brands of earphones, 3 instances each, right/left, removed and replaced twice. Measured SD was approximately 4 dB, so the error was estimated at +10 dB. This is a very conservative estimate used here because there are many unknown possible earphones.

For a given predicted pure tone average, it was assumed that the actual pure tone average could be +/−12 dB with equal probability. For a given slope, it was assumed that the actual slope could be +/−10 dB, with equal probability. Therefore each marginal cell in Table 8 would contain all the audiograms whose pure tone averages (x axis) or slopes (y axis) were within an estimated error range of predicted pure tone average or measured slope.

If a user took an In-home Test, and the data were obtained to be: Gender=Male, HSI score=24, Average Slope (R and L)=19, the predicted pure tone average is computed to as PTA=(1.23* (24)−15.4)=14. Looking up Table 8, which is for male, for the cell with slope=19 and PTA=14, it is found that the candidate audiograms are A33, A59, A47, which are the three most possible audiograms for the user. The hearing aid parameters corresponding to candidate audiograms A33, A59, A47 are then looked up in Table 6. The hearing aid parameters for A33 are then programmed to Memory 1 of a hearing aid, A59 to Memory 2, and A47 to Memory 3.

All of the methods disclosed and claimed herein can be made and executed without undue experimentation in light of the present disclosure. While systems and methods of this invention have been described in terms of preferred embodiments, it will be apparent to those of ordinary skill in the art that variations may be applied to the methods and in the steps or in the sequence of steps of the methods described herein without departing from the concept, spirit and scope of the invention. In addition, modifications may be made to the disclosed apparatuses, systems, and components. For example, components may be eliminated or substituted for the components described herein where the same or similar results would be achieved. All such similar substitutes and modifications apparent to those having ordinary skill in the art are deemed to be within the spirit, scope, and concept of the invention as defined by the appended claims.

What is claimed is:

1. A method comprising:
presenting, by a sound card, a first stimulus signal at a first frequency and a second stimulus signal at a second frequency to a user, the first frequency and the second frequency in a human audible frequency range;
receiving adjustments, from a user interface operated by the user, to the first stimulus signal and the second stimulus signal to adjust an intensity of the first stimulus signal and the second stimulus signal;
determining, by a processor, a first hearing threshold and a second hearing threshold based on the adjustments to the first stimulus signal and the second stimulus signal;
calculating, by the processor, the difference between the first hearing threshold and the second hearing threshold to yield a user threshold difference;
asking questions to the user from a questionnaire;
receiving questionnaire answers from the user;
calculating, with the processor, a user predicted pure tone average based on received questionnaire answers;
receiving, with the processor, a user age;
receiving, with the processor, a user gender;
creating, by the processor, a set of candidate audiograms, where each audiogram in the set of candidate audiograms has an associated threshold difference comprising the difference between the first hearing threshold and the second hearing threshold, an associated predicted pure tone average, an associated age, and an associated gender;
comparing, with the processor, the user threshold difference, the user predicted pure tone average, the user age, and the user gender, to the associated threshold difference, the associated predicted pure tone average, the associated age, and the associated gender associated with one or more audiograms in the set of candidate audiograms; and
selecting, with the processor, a correlated audiogram from the set of candidate audiograms whose associated threshold difference, associated predicted pure tone average, associated age, and associated gender are most closely correlated to the user threshold difference, the user predicted pure tone average, the user age, and the user gender.

2. The method of claim 1, where the first frequency is 2 kHz and the second frequency is 4 kHz.

3. The method of claim 1, wherein determining the hearing thresholds comprises:
(a) determining a first lowest level of a stimulus signal that the user can hear;
(b) determining a second lowest level of the stimulus signal that the user can hear;

(c) determining whether a difference between the first lowest level and the second lowest level is within a predetermined range; and (d) if the difference is within the predetermined range, calculating the hearing threshold, wherein the hearing threshold is based on the average of the first lowest level and the second lowest level; and (e) if the difference is out of the predetermined range, repeating the steps (a), (b), (c) and (d).

4. The method of claim 1, where calculating the difference between the first hearing threshold and the second hearing threshold further comprises calculating the range of the difference, where calculating the range of the difference further comprises:

estimating an error in the calculated difference; and determining the range of the difference based on the calculated difference and the error in the calculated difference.

5. The method of claim 1, where the questionnaire comprises the Better Hearing Institute (BHI) Questionnaire.

6. The method of claim 1, wherein the questionnaire comprises the Hearing Screening Inventory (HSI) Questionnaire.

7. The method of claim 1, further comprising programming a hearing aid for the user based on the correlated audiogram, where programming a hearing aid for the user comprises:

calculating one or more sets of hearing aid parameters based on the correlated audiogram; and storing the one or more sets of hearing aid parameters in the hearing aid.

\* \* \* \* \*

UNITED STATES PATENT AND TRADEMARK OFFICE
CERTIFICATE OF CORRECTION

PATENT NO. : 8,968,209 B2
APPLICATION NO. : 13/250781
DATED : March 3, 2015
INVENTOR(S) : Dianne J. Van Tasell It is certified that error appears in the above-identified patent and that said Letters Patent is hereby corrected as shown below:

On the title page, Item (73) Assignee, line 1:

Delete "Unitedheath" and replace with -- UnitedHealth --.

Signed and Sealed this
Fourth Day of August, 2015

Michelle K. Lee
*Director of the United States Patent and Trademark Office*